(12) United States Patent
Nicolas et al.

(10) Patent No.: US 11,540,748 B2
(45) Date of Patent: Jan. 3, 2023

(54) METHOD AND SYSTEM FOR GAIT DETECTION OF A PERSON

(71) Applicant: The Swatch Group Research and Development Ltd, Marin (CH)

(72) Inventors: Cedric Nicolas, Neuchatel (CH); Abolfazl Soltani, Lausanne (CH); Hooman Dejnabadi, Orbe (CH); Martin Savary, Yverdon-les-Bains (CH); Kamiar Aminian, La Tour-de-Peilz (CH)

(73) Assignee: The Swatch Group Research and Development Ltd, Marin (CH)

( * ) Notice: Subject to any disclaimer, the term of this patent is extended or adjusted under 35 U.S.C. 154(b) by 166 days.

(21) Appl. No.: 16/906,108

(22) Filed: Jun. 19, 2020

(65) Prior Publication Data

US 2021/0052196 A1    Feb. 25, 2021

(30) Foreign Application Priority Data

Aug. 21, 2019   (EP) .................................... 19192928

(51) Int. Cl.
*A61B 5/11*       (2006.01)
*A61B 5/00*       (2006.01)
(Continued)

(52) U.S. Cl.
CPC .............. *A61B 5/112* (2013.01); *A61B 5/681* (2013.01); *G06K 9/6232* (2013.01);
(Continued)

(58) Field of Classification Search
CPC ................... A61B 5/112; A61B 5/681; A61B 2562/0219; A61B 5/7267; A61B 5/1123;
(Continued)

(56) References Cited

U.S. PATENT DOCUMENTS 10,588,517 B2    3/2020  Chowdhary et al.
2013/0218053 A1  8/2013  Kaiser et al.
(Continued)

FOREIGN PATENT DOCUMENTS

CN    108319960 A    7/2018

OTHER PUBLICATIONS

Christine E. King & Majid Sarrafzadeh, A Survey of Smartwatches in Remote Health Monitoring, Dec. 18, 2017, J Healthc Inform Res (Year: 2017).*
Lee F. Richardson, The Sliding Window Discrete Fourier Transform, May 29, 2019, Department of Statistics and Data Science, Carnegie Mellon University (Year: 2019).*
(Continued)

*Primary Examiner* — Patrick Fernandes
(74) *Attorney, Agent, or Firm* — Oblon, McClelland, Maier & Neustadt, L.L.P.

(57) ABSTRACT

A method of detecting gaits of an individual with a sensor worn by the individual. The sensor includes an accelerometer and a processing unit. The method includes obtaining an signal representing one or more sensor acceleration values; sampling the signal to obtain a sampled signal; segmenting the sampled signal into windows to obtain a segmented acceleration signal; extracting a feature set from the segmented acceleration signal; determining a probability value, for a respective window, n, where n is a positive integer greater than zero, the probability value giving an estimated probability value of gait occurrence for the individual during the respective window; modifying the estimated probability value by using a histogram of previously detected gait durations to obtain a modified probability value; and determining, based on the modified probability value, and by using a determination threshold whether or not the respective window represents gait occurrence.

16 Claims, 3 Drawing Sheets

(51) Int. Cl.
　　　*G06K 9/62*　　　(2022.01)
　　　*G06V 10/75*　　(2022.01)
(52) U.S. Cl.
　　　CPC .........　*G06K 9/6278* (2013.01); *G06K 9/6296* (2013.01); *G06V 10/758* (2022.01); *A61B 2562/0219* (2013.01)
(58) Field of Classification Search
　　　CPC ............. A61B 5/02438; G06V 10/758; G06K 9/6232; G06K 9/6278; G06K 9/6296; G16H 50/20
　　　See application file for complete search history.

(56) References Cited

U.S. PATENT DOCUMENTS

| | | |
|---|---|---|
| 2018/0114133 A1 | 4/2018 | Chowdhary et al. |
| 2018/0333057 A1 | 11/2018 | Chowdhary et al. |
| 2019/0150793 A1 | 5/2019 | Barth et al. |

OTHER PUBLICATIONS

Blaine Reeder, Alexandria David, Health at hand: A systematic review of smart watch uses for health and wellness, Oct. 2016, Journal of Biomedical Informatics (Year: 2016).*
Kong Y. Chen and David R. Bassett, Jr, The Technology of Accelerometry-Based Activity Monitors: Current and Future, 2005, American College of Sports Medicine (Year: 2005).*
Richard P Troiano, James J McClain, Robert J Brychta, Kong Y Chen, Evolution of accelerometer methods for physical activity research, Apr. 29, 2014, Br J Sports Med (Year: 2014).*
European Search Report dated Feb. 17, 2020 in European Application 19192928.0 filed Aug. 21, 2019, (with written Opinion), 8 pages.
Pham, T. T. et al., "An Anomaly Detection Technique in Wearable Wireless Monitoring Systems for Studies of Gait Freezing in Parkinson's Disease," 2017 International Conference on Information Networking (ICOIN), IEEE, Jan. 11, 2017, pp. 41-45.

* cited by examiner

METHOD AND SYSTEM FOR GAIT DETECTION OF A PERSON

CROSS-REFERENCE TO RELATED APPLICATION

This application claims priority to European Patent Application No. 19192928.0 filed on Aug. 21, 2019, the entire disclosure of which is hereby incorporated herein by reference.

TECHNICAL FIELD

The present invention relates to a gait detection method for detecting gaits of a person. The method uses a processing circuit and an accelerometer, which may be worn on the person's wrist, for instance. The invention also relates to a gait detection sensor configured to implement the method.

BACKGROUND OF THE INVENTION

Physical activity (PA) is one of the fundamental aspects of daily life closely associated with well-being and is recognised as a leading health indicator of populations. The World Health Organization (WHO) has reported a strong connection between PA and risk of falling, cognitive function, muscular fitness, and functional health level of elderly people. PA becomes even more important when the increasing trend of aging populations is considered. PA is a crucial component in healthy aging, intervention in many treatments, and the reduction of the risk of chronic non-communicable diseases, such as diabetes, hypertension, cardiovascular diseases, depression, obesity and some types of cancer.

Amongst different types of PA, gait (e.g. walking and running) is one of the most important and effective ones whose objective assessment can provide useful and valuable information. Thanks to recent advances in wearable technologies, various systems based on inertial measurement units (IMUs), including accelerometers and gyroscopes, attached to the lower limbs, upper body or to both of these locations, have been developed to monitor PA, particularly gait bouts. In some cases, an IMU in a smartphone has been employed where the phone has been fixed to different parts of the body. While these systems provide detection of gaits outside of the laboratory, they suffer from several drawbacks. Wearing multiple sensors, for example, on foot, shank, thigh, hip, or chest, may be cumbersome, uncomfortable and awkward in daily situations, especially when long-term measurements are targeted. Fixation and alignment of the sensors with body segments to guarantee fixed orientation/location during an entire measurement may require an intervention of an expert, as well as additional tests, which affect the usability of the system or can easily disturb the wearer and modify their usual daily activities.

Moreover, the power consumption of such systems may be high due to using multiple sensors and/or modalities (e.g. a gyroscope), which limits the duration of the measurements. The existing algorithms also lack the provision of real-time data processing and analysis, relevant for generating real-time feedback, due to their high complexity. Therefore, most of the known systems operate only offline so that recorded raw data must be later transferred into a server for further analysis.

Considering the above limitations, alternative solutions for PA monitoring, particularly gait, use a single IMU mounted on the wrist. The solutions offer comfort, high usability and discreet monitoring (e.g. integrated inside a wristwatch) thus leading to an increased user compliance. The currently known wrist-based methods have used the abstract modelling where several features based on time, frequency and statistics are extracted and fed into various types of machine learning models (e.g. a decision tree or a support vector machine (SVM)). Such methods are independent of sensor orientation. Therefore, there is no need for sensor calibration and alignment. These advantages make the wrist as a suitable sensor location for long-term measurements of gait in real world situations. However, the association of the gait activity with the wrist motion is more challenging than the motion of the upper body or lower limbs. The wrist may have "independent" movements of the gait (e.g. carrying a bag, hand in pocket) and non-gait (e.g. moving wrist when sitting or standing), which cause many problems for an accurate gait detection in everyday conditions.

Nowadays, advances in the technology, as well as increasing demand and interest for long-term monitoring of physical activities, mean that a high number of consumer-oriented activity trackers, particularly smartwatches, emerge in the market. They provide a nonintrusive and easy way to track physical activities in free-living conditions. However, their reliability and validity are not yet completely known. Several studies showed a significant drop of the performance (up to 50% of error) of such commercial products under different conditions.

Regarding gait detection, one major and challenging issue is the validity of the existing methods under real-world or unsupervised conditions. In fact, most of the methods were validated only in supervised (e.g. in a controlled laboratory setting involving measurements during short periods and limited space) or semi-supervised (e.g. a series of activities lasting longer time simulating real-life situation under the supervision of an observer). Such conditions may not match real-world situations where the gait activity is context dependent, self-initiated and purposeful. Moreover, in daily life, the gait can be disturbed by "stationary" motions (e.g. shuffling around, swinging, stepping, turning, fidgeting, jumping), unpredicted sequences of PA, a huge imbalance of the data (gait periods are significantly less frequent than non-gait ones), and the presence of other types of locomotion (e.g. cycling, fitness, sport). It has been shown that the performance of PA classification significantly decreases when the validation is performed under real-life circumstances. Only few works have evaluated their methods under completely real-world conditions, without any supervisions or pre-defined sequences of PA. Those works used a subject-borne camera as a reference to label PA in free-living conditions.

SUMMARY OF THE INVENTION

An object of the present invention is to overcome at least some of the above shortcomings of the existing PA detection sensors. More specifically, the present invention aims to provide an improved gait detection method and sensor, which may be worn on a user's wrist.

According to a first aspect of the invention, there is provided a method of detecting gaits of an individual as recited in claim 1.

The present method uses an accurate and precise algorithm to detect gait bouts in completely free-living conditions using a single tri-axial accelerometer on wrist, for example. Biomechanically derived features were extracted characterising real-life gait along with using a probability estimator, such as a naïve Bayes classifier, followed by one or optionally two physically-meaningful post classification procedures to optimise the performance. The solution offers a low-power, calibration-free algorithm which needs low computation to be implemented for example inside a wristwatch which is proper for providing online feedbacks for the user in every-day situations. The algorithm has been validated under real-world conditions in healthy young and old adults against an accurate and pre-validated wearable system.

According to a second aspect of the invention, there is provided a gait detection sensor as recited in claim 13.

According to a third aspect of the invention, there is provided a wristwatch comprising the gait detection sensor according to the second aspect of the present invention.

Other aspects of the invention are recited in the dependent claims attached hereto.

BRIEF DESCRIPTION OF THE DRAWINGS

Other features and advantages of the invention will become apparent from the following description of a non-limiting example embodiment, with reference to the appended drawings, in which.

DETAILED DESCRIPTION OF THE INVENTION

Figure 1:
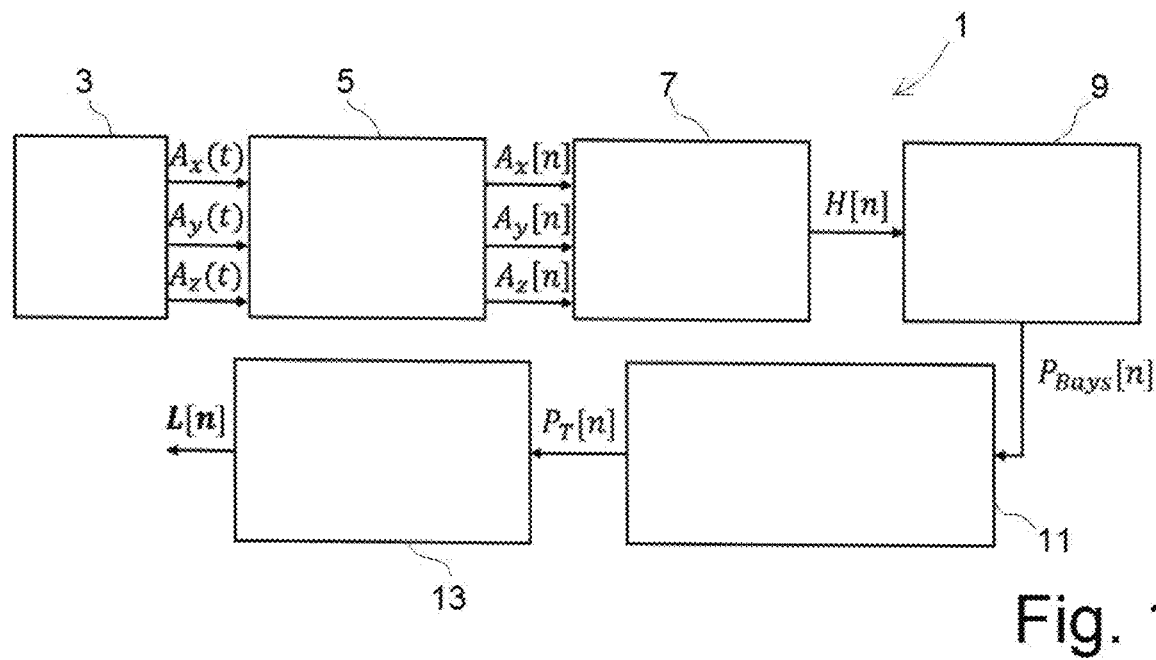
FIG. 1 is a simplified block diagram illustrating an example gait detection sensor system according to an embodiment of the present invention.

An embodiment of the present invention will now be described in detail with reference to the attached figures. The invention will be described in the context of a gait detection system using a wrist accelerometer. However, the teachings of the invention are not limited to this environment or application. For instance, the accelerometer does not have to be wrist-worn. Identical or corresponding functional and structural elements which appear in different drawings are assigned the same reference numerals. As utilised herein, "and/or" means any one or more of the items in the list joined by "and/or". As an example, "x and/or y" means any element of the three-element set {(x), (y), (x, y)}. In other words, "x and/or y" means "one or both of x and y." As another example, "x, y, and/or z" means any element of the seven-element set {(x), (y), (z), (x, y), (x, z), (y, z), (x, y, z)}. In other words, "x, y and/or z" means "one or more of x, y, and z." Furthermore, the term "comprise" is used herein as an open-ended term. This means that the object encompasses all the elements listed, but may also include additional, unnamed elements. Thus, the word "comprise" is interpreted by the broader meaning "include", "contain" or "comprehend".

FIG. 1 shows a block diagram of the proposed sensor system 1, also referred to simply as a sensor. The sensor system is in this example designed to be wrist-worn. The sensor 1 of FIG. 1 shows six functional blocks or units as explained later in more detail, namely an accelerometer 3, a segmentation unit 5, a feature extraction unit 7, a probability estimator 9, which in this example is a Bayes estimator, a temporal-based probability modification unit 11 and a smart decision making unit 13. Instead of using a Bayes estimator as the probability estimator, it would be possible to use any suitable probability estimator instead, such as a decision tree, an artificial neural network, a support vector machine etc. Furthermore, it is to be noted that the operation of these functional units could be integrated into fewer than six units. For example, the different functionalities of these blocks could all be integrated into the accelerometer 3, which in this example is configured to measure accelerations in a three-dimensional (3D) space. The measured 3D accelerometer signal $(A_x, A_y, A_z)$ from the accelerometer is fed into the segmentation unit 5, which is configured to sample and segment the accelerometer signal. The segmented signal is then fed into the feature extraction unit 7, which is arranged to extract relevant features from the segmented accelerometer signal. A feature vector H[n] (where n denotes a window number resulting from the segmentation) is then fed into the Bayes estimator 9, which is arranged to estimate the probability of gait occurrence $P_{Bayes}[n]$, and which is trained by at least some of the extracted features and their corresponding labels (gait occurrence or non-gait occurrence) from a training data set. In estimation and decision theory, a Bayes estimator or a Bayes action is an estimator or decision rule, which minimises the posterior expected value of a loss function (i.e. the posterior expected loss). Equivalently, it can be considered to maximise the posterior expectation of a utility function. An alternative way of formulating an estimator within Bayesian statistics would be maximum a posteriori estimation. An estimator can be understood to be a rule for calculating an estimate of a given quantity based on observed data. Thus, the rule (the estimator), the quantity of interest (the estimand) and its result (the estimate) can be distinguished.

The Bayes estimator is advantageously trained prior to applying the algorithm proposed below. For the training, another algorithm and sensor are advantageously used than the ones proposed in the present invention. The training data are collected from a group of individuals, such that the Bayes estimator may then be trained by following the principles of cross-validation, for instance.

The probability of gait occurrence $P_{Bayes}[n]$ is then fed into the temporal-based probability modification unit 11, which is configured to utilise temporal information of past detected activities, in this example from the training data set to modify the gait occurrence probability based on the histogram of gait durations in real-life situations. In this context by a histogram may be understood an estimate of probability distribution for gate duration or non-gate duration. The resulting probability value $P_T[n]$ is then fed into the smart decision making unit 13, which is configured to give a classification or label "gait" or "non-gait" using a smart rule according to the probability resulted from the previous steps. In the following, a more detailed description of the data processing steps is provided.

Segmentation

The segmentation unit 5 first samples the received continuous time domain acceleration signal. It is to be noted that the various acceleration signals are advantageously sampled by using the same sampling frequency, for example between 100 Hz and 1000 Hz. In this specific example, a sampling frequency of 200 Hz is used. Then, the segmentation unit 5 employs a moving window with a given time duration, in this specific example with a duration of 6 seconds, with a given time overlap, in this specific example with a 5-second overlap, to generate segmented wrist acceleration signals ($A_x[n], A_y[n], A_z[n]$), where n refers to a window number. It was experimentally found out that the window length of 6 seconds optimises the performance. The window length is thus advantageously between 1 seconds and 10 seconds or more specifically between 4 seconds and 8 seconds. This amount of data is short enough to have required time resolution and long enough to have sufficient data for frequency analysis.

Feature Extraction

A number of features were defined or identified based on biomechanics of wrist movements, such as intensity, periodicity, posture, and noisiness, to highlight intrinsic differences between gait and non-gait bouts from a wrist movement point of view. Least absolute shrinkage and selection operator (LASSO) feature selection method according to "J. Tang, S. Alelyani, and H. Liu, "Feature Selection for Classification: A Review," Data Classif. Algorithms Appl., p. 37, 2014" was used to specify the best possible feature set to optimise the performance on the training dataset. Interestingly, LASSO selected a set of features which covers all biomechanical criteria (i.e. intensity, periodicity, posture, noisiness) used to define features. Totally, 13 features were chosen in the four categories as follows:

Intensity-based features: One key difference between gait and non-gait periods is the intensity of the wrist acceleration signal. In order to extract this information, the following features were computed:

NI[n]: This is the intensity of acceleration norm calculated according to Equation 1.

$$NI[n] = \log_{10}\left(\frac{1}{N}\sum_{i=1}^{N} SA[f_i]\right), \quad (1)$$

where $SA[f_i]$ is the amplitude of spectrum acceleration norm computed according to Equations 2 and 3. In order to estimate the spectrum, N-point Fast Fourier Transform (FFT) with Blackman windowing was used, where N is the number of samples within a time window (i.e. N=1200 in the present case). Moreover, $f_i$ refers to frequency resolution of the method which is shown in Equation 4. A logarithmic function was used in order to shorten the range of this feature, as well as heavy tail of its histogram, which is proper for further Bayesian modelling.

$$SA[f] = |FFT(A[n])| \quad (2)$$

$$A[n] = \sqrt{A_x[n]^2 + A_y[n]^2 + A_z[n]^2} \quad (3)$$

$$f_i = \{0, 0.17, 0.34, \ldots, 100\} \, 1 \le i \le 1200 \quad (4)$$

MeanA[n]: This is mean value of acceleration norm within a time window.

Periodicity-based features: Considering the cyclic nature of the gait, 5 features related to the periodicity of acceleration signals was included as follows:

NACFmax[n]: Autocorrelation function of acceleration norm computed and normalised to the first sample (i.e. sample of zero lag). Then, its maximum peak, NACFmax, excluding the zero lag sample, was reported for each window. This feature may thus be called maximum peak of normalised autocorrelation function of acceleration norm.

NACFp2p[n]: This feature is the peak-to-peak value of maximum peak and valley of the normalised autocorrelation function, excluding the zero lag sample. In other words, this feature is peak-to-peak value of normalised autocorrelation function of acceleration norm.

SAmax[n]: Normalised spectrum of acceleration norm (NSA) was estimated using $SA[f_i]$ according to Equation 5 and its maximum peak amplitude was computed as SAmax[n]. This feature is thus maximum peak of spectrum of acceleration norm.

$$NSA[f_i] = \frac{SA[f_i]}{\sum_{j=1}^{N} SA[f_i]} \quad (5)$$

DomSAmax[n]: A score was designed which showed how much the maximum peak of NSA was sharp compared to its neighbouring samples. This score can be called a sharpness of the maximum peak of NSA. This feature was computed according to Equation 6, where $f_{max}$, $f_{max-1}$ and $f_{max+1}$ refer to the frequencies of maximum peak of NSA, a sample before and after, respectively. This feature is thus sharpness of maximum peak of spectrum of acceleration norm.

$$DomSAmax[n] = \frac{NSA[f_{max}]}{\sum_{f=\{f_{max-1}, f_{max}, f_{max+1}\}} NSA[f]} \quad (6)$$

Cad[n]: Not only the periodicity of the signal, but also the value of the period itself is an important piece of information to distinguish between gait and non-gait periods. Generally, stride frequency (i.e. fundamental frequency of the gait signal) is bounded in a short range around 1 Hz (i.e. between 0.3 Hz and 2.5 Hz). The fundamental frequency of acceleration signal was computed using the algorithm presented in "B. Fasel et al., "A wrist sensor and algorithm to determine instantaneous walking cadence and speed in daily life walking," Med. Biol. Eng. Comput., vol. 55, pp. 1773-1785, 2017". This feature is thus cadence or step frequency (steps/min) of gait.

Figure 2:
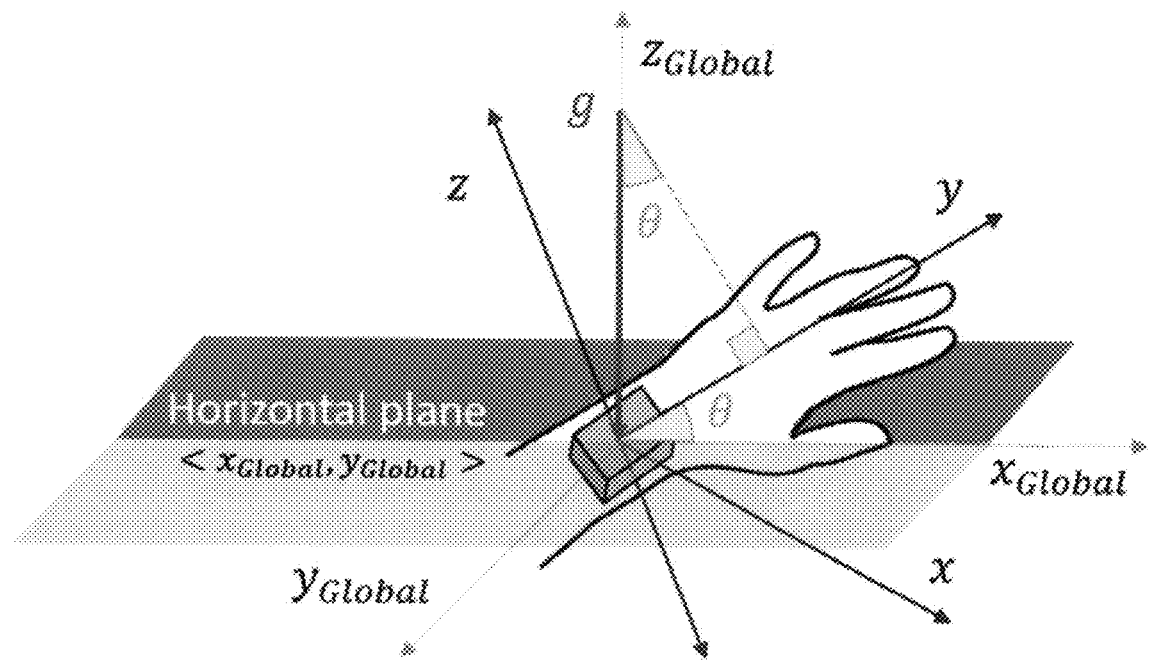
FIG. 2 schematically illustrates how wrist posture may be defined in the context of the present invention.

Posture-based features: During gait (i.e. running or walking), the wrist generally has a specific predictable posture, while during non-gait periods, the posture is mainly unpredictable and irregular. Consequently, extracting information about the posture of the wrist should be useful for gait bouts detection. We defined θ as the angle between y-axis of the accelerometer on the wrist and the global horizontal plane $<x_{Global}, y_{Global}>$ (the plane made by x and y axes of the global coordinate system and perpendicular to the gravity vector, see FIG. 2). By assuming that the sensor can only turn around the wrist, y-axis of the sensor was almost aligned with the longitudinal axis of the wrist. According to FIG. 2 and if the dynamic acceleration of the wrist movement remains low, the projection of gravity vector on y-axis of accelerometer and the plane defined by x-axis and z-axis of the sensor ($<x, z>$) are:

$$A_y[n] = g \sin(\theta[n]) \quad (7)$$

$$A_{<x,z>}[n] = \sqrt{A_x[n]^2 + A_z[n]^2} = g \cos(\theta[n]), \quad (8)$$

where g denotes the gravity acceleration, and $A_{<x,z>}[n]$ is the amplitude of resultant acceleration vector on the plane $<x, z>$ for window n. Consequently, the angle θ[n] can be estimated through Equation 9.

$$\theta[n] = \arctan\left(\frac{A_y[n]}{\sqrt{A_x[n]^2 + A_z[n]^2}}\right) \quad (9)$$

The proposed postured-based feature, i.e. the posture of the wrist, is defined as:

$$WristPost[n] = mean(sin(\theta[n])) \quad (10)$$

Noisiness-based features: In gait, acceleration signal is pseudo-cyclic with energy mostly in the low frequency band, while in non-gait periods the signal is rather random and erratic with energy distributed in a larger frequency band. Therefore, like signal-to-noise ratio (SNR), the gait/non-gait power ratio is expected to be higher during gait than non-gait periods. Consequently, several features were devised to capture information about the level of "noise" (i.e. non-gait period) in the signal (i.e. gait period). These features are as follow:

HLR[n]=high to low frequency ratio: We defined the ratio between the intensities present at high frequencies and at low frequencies as a feature according to Equation 11. The frequency threshold was experimentally set to 3.5 Hz to optimise the performance However, it is possible to use another frequency threshold instead. The threshold is advantageously between 1 Hz and 10 Hz or more specifically between 2 Hz and 5 Hz. This feature is thus high to low frequencies ratio of energy of acceleration norm.

$$HLR[n] = \frac{\sum_{f_i \geq 3.5\,Hz} SA[f_i]}{\sum_{0 < f_i < 3.5\,Hz} SA[f_i]} \quad (11)$$

ZCR[n]: Zero crossing rate should be higher in acceleration norm during non-gait period due to noisy and erratic nature of wrist movements. First, mean value of the acceleration norm within the time window was removed. Then, any linear trends in the resulted signal were discarded, for instance by using "deterend" function in MATLAB®. Eventually, the number of zero crosses was counted as feature ZCR[n]. This feature is thus zero crossing rate of mean-removed acceleration norm.

SEF[n]: As it is shown in Equation 12, spectral edge frequency estimates the frequency where a (%) of the energy of the signal is observed below that frequency "J. C. Drummond, C. A. Brann, D. E. Perkins, and D. E. Wolfe, "A comparison of median frequency, spectral edge frequency, a frequency band power ratio, total power, and dominance shift in the determination of depth of anesthesia," Acta Anaesthesiol. Scand., vol. 35, no. 8, pp. 693-699, 1991". We found that $\alpha=70(\%)$ provided the best performance in the present application. This feature may be called spectral edge frequency of acceleration norm.

$$SEF[n] = \min_{f_i}\left(\left|\sum_{j=1}^{i} NSA[f_i] - \frac{\alpha}{100}\right|\right) \quad (12)$$

RandA[n]: By assuming that the wrist acceleration signal is less random during gait than non-gait periods, we defined RandA[n] feature according to an autocorrelation-based test presented in "P. J. Brockwell, R. A. Davis, and M. V. Calder, Introduction to time series and forecasting, vol. 2. Springer, 2002" to measure how much the signal is random. According to this test, if a time series comes from a stationary random process (which is almost the case for acceleration norm of non-gait periods within a short window of 6 seconds), samples of autocorrelation of the time series will be mainly bounded between $\pm 1.96/\sqrt{N}$ thresholds where N is the number of samples within a time window (i.e. 1200). We defined RandA[n] as the percentage of autocorrelation samples outside the range of $\pm 1.96/\sqrt{N}$. The higher the value of RandA[n] is, the less random the signal is. This feature may thus be defined as randomness score of acceleration norm.

KurtosisA[n]: Kurtosis is a well-known tool to measure how much the distribution of data is outlier-prone "P. H. Westfall, "Kurtosis as peakedness, 1905-2014. RIP," Am. Stat., vol. 68, no. 3, pp. 191-195, 2014". We hypothesized that the acceleration norm of non-gait periods contains more outliers than gait due to higher randomness of the signal. Therefore, the kurtosis of the acceleration norm within a time window was computed as a feature.

Eventually, for each time window n, H[n] was built as the feature vector including all selected features. However, it would be possible to include in the feature vector only some of the above features or even some other features in addition or instead.

Bayes Estimator

The probability of gait occurrence for each window was estimated by using the Bayes estimator according to Equation 13:

$$P_{Bayes}[n] = P_{G|H[n]} = \frac{P_G P_{H[n]|G}}{P_G P_{H[n]|G} + P_{NG} P_{H[n]|NG}}, \quad (13)$$

where $P_{G|H[n]}$ is the probability of gait occurrence condition on the observed feature vector, H[n]. In addition, $P_{H[n]|G}$ and $P_{H[n]|NG}$ are probabilities of occurrence of having H[n] in gait (G) class and non-gait (NG) class, respectively. Furthermore, $P_G$ and $P_{NG}$ are respectively prior probabilities of gait and non-gait happening. We considered multivariate multinomial distributions ("mvmn" in MATLAB®) for the Bayes estimator. Furthermore, in order to manage the intrinsic imbalances of samples between gait and non-gait periods (in real-world situations, non-gait samples are relatively more frequent than gait ones), we took advantage of Laplace smoothing parameter, "A. Y. Liu and C. E. Martin, "Smoothing multinomial naïve bayes in the presence of imbalance," in International Workshop on Machine Learning and Data Mining in Pattern Recognition, 2011, pp. 46-59", in computation of the prior probabilities as follows:

$$P_G = \frac{N_G + l}{N_G + N_{NG} + 2l} \quad (14)$$

$$P_{NG} = \frac{N_{NG} + l}{N_G + N_{NG} + 2l}, \quad (15)$$

where $N_{NG}$, and $N_G$ are the total number of samples or windows observed for non-gait and gait periods. l is a smoothing parameter fixed empirically to $(N_G-N_{NG})/10$.

Temporal-Based Probability Modification

Figure 3:
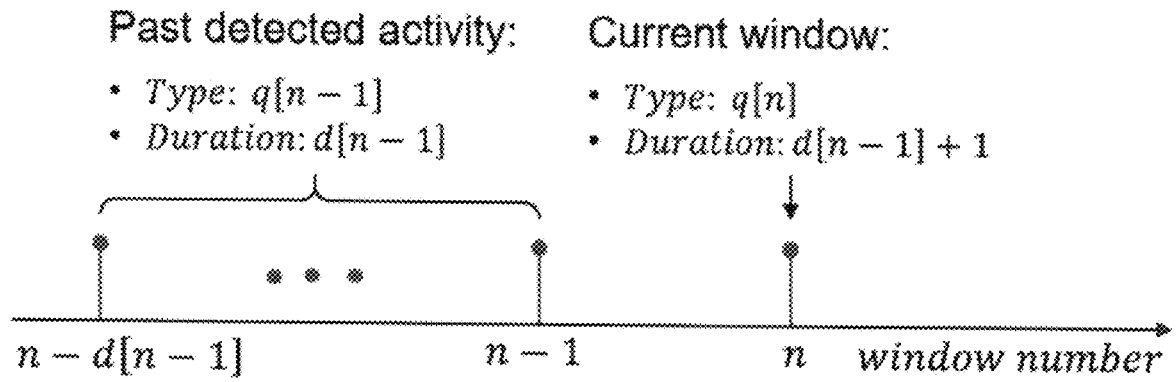
FIG. 3 is a graph illustrating definitions for temporal-based probability modification, which is used in the process of detecting gaits according to the present invention.

We took advantage of information of past detected activities to increase the certainty of the decision made for the current activity. As shown in FIG. 3, let us define q[n−1] and d[n−1] as the type and the duration of the last activity, respectively, detected up to window n−1 (i.e. the last activity was started from window n−d[n−1] and lasted up to window n−1 included) and $P_{q[n]=q[n-1]|d[n-1]}$ denotes the probability of having the same activity in window n (i.e. q[n]=q[n−1]) as in the previous window, knowing the type (q[n−1]) and duration (d[n−1]) of the last activity. To this end, two exponential functions (see Equations 16 and 17) were fitted into probability density functions of duration of gait and non-gait bouts in daily life, obtained from the training session of the method. Parameters (i.e. $\beta_G$, $\gamma_G$, $\tau_G$, etc.) in Equations 16 and 17 are thus obtained from the respective histogram of gait durations and non-gait durations, respectively. Then, since the probability given by Bayes ($P_{Bayes}$) was generally more reliable than $P_{q[n]=q[n-1]|d[n-1]}$ due to using several features obtained from the acceleration signal, the modification effect of $P_{q[n]=q[n-1]|d[n-1]}$ was reduced by mapping that into a shorter range of [0.05, 0.20] (experimentally adjusted) by using Equation 18 to obtain $\tilde{P}_{q[n]=q[n-1]|d[n-1]}$. However, another suitable range could be used instead. Eventually, the modified probability of gait occurrence ($P_T$) of time window n was computed by using Equation 19, where "min-max" function was used to limit the probability to the range of [0,1].

$$P_{q[n]=G|d[n-1]} = \beta_G e^{-\tau_G(d[n-1]+1)} + \gamma_G e^{-\rho_G(d[n-1]+1)} \quad (16)$$

$$P_{q[n]=NG|d[n-1]} = \beta_{NG} e^{-\tau_{NG}(d[n-1]+1)} + \gamma_{NG} e^{-\rho_{NG}(d[n-1]+1)} \quad (17)$$

$$\tilde{P}_{q[n]=q[n-1]|d[n-1]} = 0.15 P_{q[n]=q[n-1]|d[n-1]} + 0.05 \quad (18)$$

$$P_T[n] = \min(\max(P_{Bayes}[n] + \psi \tilde{P}_{q[n]=q[n-1]|d[n-1]}, 0), 1), \quad (19)$$

where $\psi$ was defined as follows:

$$\psi = \begin{cases} +1, & q = G \\ -1, & q = NG \end{cases} \quad (20)$$

Smart Decision Making

Figure 4:
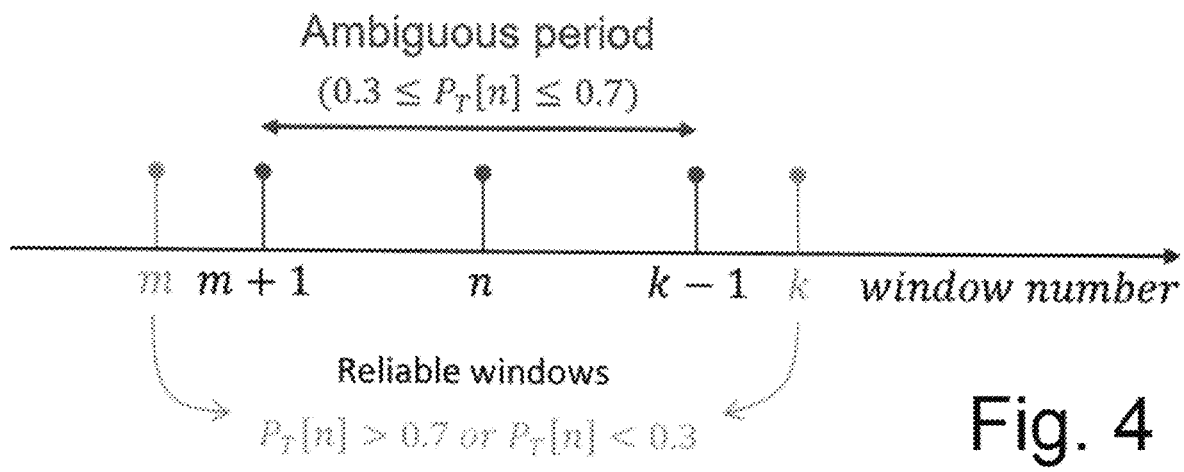
FIG. 4 is a graph illustrating definitions for smart decision making, which may be used in the process of detecting gaits according to the present invention.

When $P_T[n]$ is far enough from 0.5, it is easy to decide if the activity of the window n is gait or not. However, making the decision is challenging when $P_T[n]$ is close to 0.5, which can happen in the proximity of transients between the activities since a part of the feature window is gait and the other part is non-gait. Consequently, the following algorithm was designed to make a smart decision based on $P_T[n]$. If $P_T[n]<0.3$ and $P_T[n]>0.7$, the decisions were $N_G$ and G, respectively. Here, the decision refers to the label L [n] for the current window n. These windows can be called reliable windows. On the other hand, if $0.3 \leq P_T[n] \leq 0.7$ (called ambiguous windows or uncertainty zone), then we checked the period, or more specifically its duration, between the last and next reliable windows. For instance, for ambiguous window n, windows m and k are the last and next reliable windows, respectively (m<n<k, see FIG. 4). If k−m+1≤10, then the threshold of decision making was changed from conventional 0.5 to 1−mean($P_T[m<n<k]$). Otherwise, decisions were G and $N_G$ if $P_T[n]>0.6$ or $P_T[n]<0.4$, respectively and for $0.4 \leq P_T[n] \leq 0.6$, the last reliable decision was assigned to window n (i.e. L[n]=L[m]). It is to be noted that other suitable parameter values could be used instead of the above parameter values. The algorithm below briefly explains the procedure of the proposed smart decision making.

```
START
IF P_T[n] > 0.7, THEN L[n] = G
IF P_T[n] < 0.3, THEN L[n] = NG
IF 0.3 ≤ P_T[n] ≤ 0.7, THEN
    IF k − m + 1 ≤ 10, THEN
        IF L[m] = L[k], THEN L[n] = L[m] = L[k]
        ELSE, THEN
            IF P_T[n] > 1 − mean(P_T[m < n < k]), THEN L[n] = G
            ELSE, THEN L[n] = NG
```

```
ELSE IF k − m + 1 > 10
    IF P_T[n] > 0.6, THEN L[n] = G
    ELSE IF P_T[n] < 0.4, THEN L[n] = NG
    ELSE L[n] = L[m]
END
```

Figure 5:
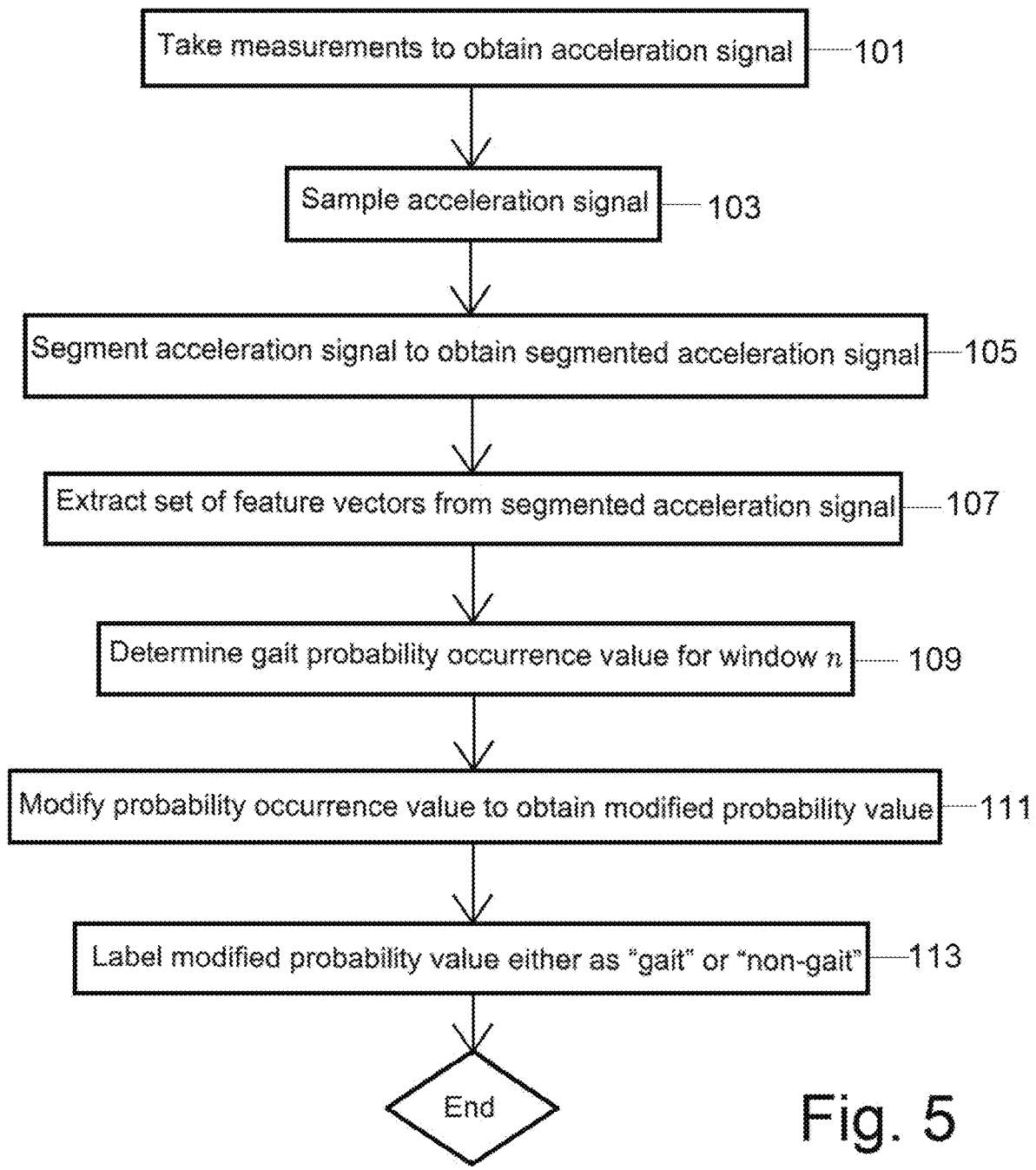
FIG. 5 is a flow chart summarising the method steps of an example process of detecting gaits according to the present invention.

The above process is summarised in the flow chart of FIG. 5. In step 101, the accelerometer 3 takes measurements to obtain one or more acceleration signals, which are continuous signals in the time domain. In step 103, the segmentation unit 5 samples these continuous time domain signals and in step 105 segments them. In step 107, the feature extraction unit 7 extracts a set of feature vectors from the segmented acceleration signal for a respective window. In step 109, the Bayes estimator 9 uses the extracted feature set and determines a gait probability occurrence value for the respective window. In step 111, the temporal-based probability modification unit 11 modifies the probability value obtained in step 109 to improve the precision of the probability value. In step 113, the smart decision making unit 13 labels the modified probability value obtained in step 111. The modified probability value is labelled either as "gait" or "non-gait". It is to be noted that the smart decision making unit 13 is optional and the label could be derived from the modified probability value directly for instance so that a (modified) probability value greater than 0.5 would be interpreted as "gait", while other probability values would be labelled as "non-gait".

The principles of an accurate and precise window-based algorithm were explained above to recognise gait bouts and estimate their duration using a single low-power accelerometer mounted on the wrist in unsupervised real-world situations. Probability density functions of the biomechanically-derived features (according to i.e. intensity, periodicity, posture, and noisiness) illustrate a high ability for the selected features to distinguish between gait and non-gait bouts. The LASSO scores show that NACFmax, SAmax, NI and WristPost are among the best or meaningful features in this application. In addition, the periodicity was a better criterion for distinguishing between gait and non-gait bouts.

Using only one low-power accelerometer, optimising features computation and using some implementation techniques, an optimised implementation of the proposed sensor showed a very low power consumption (135.5 mAh per year) in real-world conditions. The implemented method offers around one year of continuous effective measurement of gait with a primary normal battery cell (250 mAh). This is a great advantage since many medical and sport applications crucially need long-term measurements of physical activities in real-life situations. The simplicity of the proposed method and its low computation time (1 ms per window) offers the possibility of a real-time and on-board analysis of physical activities which provides the possibility of generating real-time feedback that can be important in many applications, such as intervention programs.

The proposed method, validated in unsupervised daily situations over young and elderly people, offers a high potential to be used in clinical settings for the monitoring of patients with activity restrictions due to diseases. As an example, the system may be used among a large population of older adults to analyse the effect of various factors such as aging, obesity, and frailty on the quality and quantity of physical activities in daily life situations. More importantly, the proposed method can be used as a primary stage for many algorithms in the analysis of physical activities, where accurate detection of gait bouts is needed, such as gait cadence estimation, and gait speed estimation.

To conclude, the present invention in the above example presented an accurate and precise method for detection of gait bouts in free-living situations. Biomechanically-derived features were integrated with a naïve Bayes classifier followed by two physically-meaningful post-classification steps to deal with the difficulties posed by challenging movements of the wrist in real-world situations. Such a wrist-based, low-power, and calibration-free (no calibration phase is needed for sensor-to-body alignment) system offers a versatile measurement tool with high usability and autonomy, perfect for long-term monitoring of physical activities in free-living situations. In addition, the simplicity of the proposed method and being real-time allows implementing the method inside a wristwatch, which protects privacy of the user. This also provides the possibility of giving online meaningful feedback to the user in daily life to promote a more active life-style.

While the invention has been illustrated and described in detail in the drawings and foregoing description, such illustration and description are to be considered illustrative or exemplary and not restrictive, the invention being not limited to the disclosed embodiment. Other embodiments and variants are understood, and can be achieved by those skilled in the art when carrying out the claimed invention, based on a study of the drawings, the disclosure and the appended claims.

In the claims, the word "comprising" does not exclude other elements or steps, and the indefinite article "a" or "an" does not exclude a plurality. The mere fact that different features are recited in mutually different dependent claims does not indicate that a combination of these features cannot be advantageously used. Any reference signs in the claims should not be construed as limiting the scope of the invention.

What is claimed is:

1. A method of detecting gaits of an individual by using a gait detection sensor mounted on a wristwatch and worn by the individual, the gait detection sensor comprising an accelerometer and processing circuitry, the method comprising:
   obtaining, by the accelerometer of the gait detection sensor, an acceleration signal representing one or more sensor acceleration values;
   sampling, by the processing circuitry of the gait detection sensor, the acceleration signal to obtain a sampled acceleration signal;
   segmenting, by the processing circuitry of the gait detection sensor, the sampled acceleration signal into a given number of windows of a given duration to obtain a segmented acceleration signal;
   extracting, by the processing circuitry of the gait detection sensor, a feature set from the segmented acceleration signal, the feature set characterising the acceleration signal;
   determining, by the processing circuitry of the gait detection sensor, a probability value using a trained probability estimator using the extracted feature set, for a respective window, n, where n is a positive integer greater than zero, the probability value giving an estimated probability value of gait occurrence for the individual during the respective window;
   modifying, by the processing circuitry of the gait detection sensor, the estimated probability value by using a histogram of previously detected gait durations to obtain a modified probability value;
   determining, by the processing circuitry of the gait detection sensor, based on the modified probability value, and by using a determination threshold whether or not the respective window represents gait occurrence; and
   displaying the gait occurrence or non-gait occurrence on the wristwatch, wherein the modified probability value is obtained as:

$$P_T[n]=\min(\max(P_{Bayes}[n]+\psi \tilde{P}_{q[n]=q[n-1]d[n-1]},0),1),$$

where $P_{Bayes}[n]$ is the estimated probability value of gait occurrence for the individual during the respective window, $\tilde{P}_{q[n]=q[n-1]d[n-1]}$ is a probability with a range smaller than 1 of having the same gait activity in window n as in the previous window n−1, d denotes activity duration, q denotes activity type, and $$\psi = \begin{cases} +1, q = \text{gait} \\ -1, q = \text{nongait} \end{cases}.$$

2. The method according to claim 1, wherein the probability estimator comprises a Bayes estimator.

3. The method according to claim 1, wherein
   the extracted feature set comprises at least one of the following feature categories: intensity of the acceleration signal, periodicity of the acceleration signal, posture of the individual at a sensor location, and noisiness of the acceleration signal, and
   at least one of the feature categories comprises one or more biomechanical features.

4. The method according to claim 3, wherein the one or more biomechanical features comprise at least one of the following features: intensity of acceleration norm, mean of acceleration norm, maximum peak of normalised autocorrelation function of acceleration norm, peak-to-peak value of normalised autocorrelation function of acceleration norm, maximum peak of spectrum of acceleration norm, sharpness of maximum peak of spectrum of acceleration norm, step frequency of gait, posture of the individual at a sensor location, ratio of energy of high to low frequencies of acceleration norm, zero crossing rate of mean-removed acceleration norm, spectral edge frequency of acceleration norm, randomness score of acceleration norm, and kurtosis of acceleration norm.

5. The method according to claim 1, wherein the segmented acceleration signal comprises three substantially orthogonal acceleration components ($A_x[n]$, $A_y[n]$, $A_z[n]$).

6. The method according to claim 1, further comprising training the probability estimator by using a training data set prior to determining the estimated probability value.

7. The method according to claim 1, wherein the accelerometer is worn on a wrist of the individual.

8. The method according to claim 1, wherein the determination is made based on the acceleration signal from a single accelerometer only.

9. A method of detecting gaits of an individual by using a gait detection sensor mounted on a wristwatch and worn by the individual, the gait detection sensor comprising an accelerometer and processing circuitry, the method comprising:
   obtaining, by the accelerometer of the gait detection sensor, an acceleration signal representing one or more sensor acceleration values;
   sampling, by the processing circuitry of the gait detection sensor, the acceleration signal to obtain a sampled acceleration signal;

segmenting, by the processing circuitry of the gait detection sensor, the sampled acceleration signal into a given number of windows of a given duration to obtain a segmented acceleration signal;

extracting, by the processing circuitry of the gait detection sensor, a feature set from the segmented acceleration signal, the feature set characterising the acceleration signal;

determining, by the processing circuitry of the gait detection sensor, a probability value using a trained probability estimator using the extracted feature set, for a respective window, n, where n is a positive integer greater than zero, the probability value giving an estimated probability value of gait occurrence for the individual during the respective window;

modifying, by the processing circuitry of the gait detection sensor, the estimated probability value by using a histogram of previously detected gait durations to obtain a modified probability value;

determining, by the processing circuitry of the gait detection sensor, based on the modified probability value, and by using a determination threshold whether or not the respective window represents gait occurrence; and displaying the gait occurrence or non-gait occurrence on the wristwatch, wherein if the modified probability value, $P_T[n]$, is determined to be in an ambiguous zone, such that $a \leq P_T[n] \leq (1-a)$, then the processing circuitry checks a period duration between a last non-ambiguous window, m, and a next non-ambiguous window, k, such that m<n<k, in the non-ambiguous window $P_T[n]>1-a$, or $P_T[n]<a$, then if $k-m+1 \leq b$, where b is a positive integer, then the determination threshold is changed from 0.5 to $1-\text{mean}(P_T[m<n<k])$.

10. The method according to claim 9, wherein a is between 0.1 and 0.3, while b is between 5 and 15.

11. The method according to claim 9, wherein if the condition $k-m+1 \leq b$ is not fulfilled, the determination threshold is set to $0.5+c$ for gait occurrence, and is set to $0.5-c$ for non-gait occurrence such that gait is determined to occur if $P_T[n] > (0.5+c)$, while non-gait is determined to occur if $P_T[n] < (0.5-c)$, and for $(0.5-c) \leq P_T[n] \leq (0.5+c)$, the last non-ambiguous determination is assigned to window n.

12. The method according to claim 11, wherein c is between 0.02 and 0.2.

13. The method according to claim 10, wherein a is between 0.15 and 0.25.

14. The method according to claim 10, wherein b is between 8 and 12.

15. The method according to claim 12, wherein c is between 0.05 and 0.15.

16. A gait detection sensor for detecting gaits of an individual mounted on a wristwatch and worn by the individual, the gait detection sensor comprising:

an accelerometer configured to obtain an acceleration signal representing one or more sensor acceleration values; and processing circuitry configured to sample the acceleration signal to obtain a sampled acceleration signal, segment the sampled acceleration signal into a given number of windows of a given duration to obtain a segmented acceleration signal, extract a feature set from the segmented acceleration signal, the feature set characterising the acceleration signal, detect a probability value, by using a trained probability estimator using the extracted feature set, for a respective window, n, where n is a positive integer greater than zero, the probability value giving an estimated probability value of gait occurrence for the individual during the respective window, modify the estimated probability value by using a histogram of previously detected gait durations to obtain a modified probability value, and detect, based on the modified probability value, and by using a determination threshold whether or not the respective window represents gait occurrence, the gait occurrence or non-gait occurrence being displayed on the wristwatch, wherein the modified probability value is obtained as:

$$P_T[n] = \min(\max(P_{Bayes}[n] + \psi \tilde{P}_{q[n]=q[n-1]d[n-1]}, 0), 1),$$

where $P_{Bayes}[n]$ is the estimated probability value of gait occurrence for the individual during the respective window, $\tilde{P}_{q[n]=q[n-1]d[n-1]}$ is a probability with a range smaller than 1 of having the same gait activity in window n as in the previous window n−1, d denotes activity duration, q denotes activity type, and $$\psi = \begin{cases} +1, & q = \text{gait} \\ -1, & q = \text{nongait} \end{cases}.$$

* * * * *